(12) United States Patent
Whaley

(10) Patent No.: US 7,717,891 B1
(45) Date of Patent: May 18, 2010

(54) PORTABLE COLLECTION AND CLEANSING DEVICE

(76) Inventor: Linda J. Whaley, 524 Bright Angel Rd., Desoto, TX (US) 75115

(*) Notice: Subject to any disclaimer, the term of this patent is extended or adjusted under 35 U.S.C. 154(b) by 1327 days.

(21) Appl. No.: 11/190,517

(22) Filed: Jul. 28, 2005

(51) Int. Cl.
*A61M 1/00* (2006.01)
(52) U.S. Cl. .................. 604/319; 604/317; 604/322
(58) Field of Classification Search ......... 604/317–323; 4/144.1, 144.2, 463, 469, 476, 479, 615, 4/616
See application file for complete search history.

(56) References Cited

U.S. PATENT DOCUMENTS

| | | | |
|---|---|---|---|
| 2,944,551 A | | 7/1960 | Breer |
| 3,626,941 A | | 12/1971 | Webb |
| 3,690,555 A | | 9/1972 | Johnson |
| D268,525 S | | 4/1983 | Andersen et al. |
| 5,042,193 A | * | 8/1991 | Steiner ................. 43/54.1 |
| 5,350,369 A | * | 9/1994 | Workman et al. ........... 604/327 |
| 5,363,980 A | * | 11/1994 | Mulcahy ................. 220/495.07 |
| 5,425,468 A | * | 6/1995 | Birkel et al. ............ 220/495.11 |
| 5,511,682 A | * | 4/1996 | Pace ......................... 280/47.26 |
| 6,238,378 B1 | * | 5/2001 | Perez ........................ 604/317 |
| 6,311,339 B1 | | 11/2001 | Kraus |
| 6,395,011 B1 | * | 5/2002 | Johanson et al. ............ 606/179 |
| 6,652,495 B1 | * | 11/2003 | Walker ....................... 604/319 |
| 6,770,060 B2 | | 8/2004 | Hoenig |

* cited by examiner

*Primary Examiner*—Melanie J Hand

(57) ABSTRACT

A device includes a housing that can be transported between remote locations. The housing includes base and cover members conjoined therewith. The base member includes an open top end and a divider position in a cavity thereof, defining isolated chambers within the housing. The cover member includes a divider mateable with the divider of the base member. A mechanism is included for locking the cover member to the base member. A mechanism is included for collecting body excrements from the patient and is in fluid communication with one of the chambers. A mechanism is included for cleansing a selected portion of the patient and is in fluid communication with another chamber. The cleansing mechanism and the collecting mechanism are independently and simultaneously operable, and are electrically mated to an external power supply source.

6 Claims, 6 Drawing Sheets

PORTABLE COLLECTION AND CLEANSING DEVICE

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to collection and cleansing devices and, more particularly, to a portable collecting and cleansing device for collecting body excrements and promoting hygiene for bed-ridden patients.

2. Prior Art

Accommodating the physiological necessity to urinate or defecate on the part of incapacitated or infirm patients is problematical. Proposed solutions to this need have demonstrated that it is an illusive problem. The ubiquitous bedpan generally has been employed for this procedure. However, where the patient is severely incapacitated, for example, in recovery from stroke and the like, the procedure is highly physically taxing both on the part of the patient and the medical attendant.

The most prevalent care for person so disposed is to apply diaper-like absorbing material or diapers to contain or absorb solid and fluid excrement, respectively. However, this requires much attention from a nurse or attendant and is extremely uncomfortable for the physically impaired person. This is especially true in cases where the discharge of excrement is constant because complete cessation of bowel and urination control has been lost.

A number of prior art devices are known for collecting and storing fluid and solid excrement. Although such collecting and storing devices are sufficient for their intended applications they still have various drawbacks. The greatest limitation of current collecting devices is the considerable weight and size associated with these devices. Often times, people reach a point in the course of their rehabilitation where movement by their own accord is possible. However, they are still dependent on the collecting device that has such a considerable weight that the device effectively prevents them from becoming mobile again.

Accordingly, a need remains for a portable collection and cleansing device in order to overcome the above-noted shortcomings. The present invention satisfies such a need by providing a portable collection and cleansing device that is convenient and easy to use, is practical in design, and provides healthful benefits to the user and their caretaker(s). Such a device is appealing to a wide range of people and is utilized by bedridden as a convenient alternative to catheterization or adult diapers. The user benefits from the waste storage and disposal device that offers hygiene benefits as well. Such a device also reduces or eliminates the need for constant assistance, which aids in providing the individual with a higher level of sufficiency and self-esteem.

BRIEF SUMMARY OF THE INVENTION

In view of the foregoing background, it is therefore an object of the present invention to provide a portable collection and cleansing device. These and other objects, features, and advantages of the invention are provided by a portable device for collecting body excrements and promoting hygiene for bed-ridden patients.

The device includes a housing that is suitably sized and shaped for advantageously and conveniently being transported between remote locations by an operator. Such a housing includes a base member and a cover member removably conjoinable directly therewith. The base member includes an open top end and further includes a linear divider centrally position within a cavity of the base member for effectively defining a pair of isolated and coextensively shaped chambers within the housing. The cover member includes a divider directly mateable with the divider of the base member when the cover member is attached to the base member.

A mechanism is included for locking the cover member to the base member such that one of the chambers effectively maintains a constant air pressure level greater than an ambient air pressure level surrounding the one chamber. Such a mating mechanism preferably includes a plurality of fasteners threadably connected directly to the threaded outer surface of the primary conduit such that the primary conduit is advantageously and effectively prohibited from telescopically sliding through the cover member. A clamp is directly positioned about the flanged end portion of the primary conduit. Such a clamp biases the flanged portion to a compressed position, effectively crimping the primary conduit about the auxiliary conduit.

A mechanism is included for collecting body excrements from the patient. Such a collecting mechanism is in fluid communication with another one of the chambers wherein the body excrements are advantageously automatically deposited therein without directly contacting a caregiver. The collecting mechanism preferably includes a waste container removably positional within the another chamber and a disposable waste bag removably nested within the waste container. Such a waste bag is formed from fluid-impermeable material.

A primary conduit is formed from deformably resilient material and is channeled through the cover member. Such a primary conduit has a linear shape and axially opposed end portions seated within the waste bag and disposed exterior of the cover member. The primary conduit has a threaded outer portion confronting the cover member and has a flanged upper end portion situated to an exterior of the housing. An auxiliary conduit is formed from disposable material and has opposed end portions seated within the waste bag and disposed to an exterior of the cover member respectively. The primary conduit includes mechanism for statically mating with the auxiliary conduit such that the primary and auxiliary conduits remain in fluid communication during operating conditions.

The collecting mechanism may further include a funnel-shaped suction nozzle formed from disposable material and removably attached to a distal end portion of the auxiliary conduit. An air pump is directly and operably coupled to the primary conduit. Such an air pump is seated within the housing and selectively adaptable between operating and non-operating modes for facilitating the removal of body excrements from the patient.

A mechanism is included for cleansing a selected portion of the patient. Such a cleansing mechanism is in fluid communication with the one chamber. The cleansing mechanism and the collecting mechanism are independently and simultaneously operable such that a group of care givers can contemporaneously service the patient. The collecting and cleansing mechanism are further electrically mated to an external power supply source. The cleansing mechanism preferably includes a collapsible vessel seated within the one chamber. Such a vessel contains a predetermined quantity of fluid maintained at the air pressure level. An air supply source is mated within the housing and includes a conduit in fluid communication with an interior of the vessel.

Such a conduit has a bottom end portion positioned above a water line of the vessel. A primary conduit has opposed end portions submerged within the vessel and disposed exterior of housing respectively. An auxiliary conduit is in fluid communication with the primary conduit for advantageously and effectively directing fluid away from the housing. A trigger-actuated discharge nozzle is directly connected to the auxiliary conduit wherein an exit flow rate of the fluid can conveniently be controlled at a greater speed than a flow rate of the fluid entering the primary conduit. Such a discharge nozzle includes a scrubbing pad removably attached directly thereto. The scrubbing pad is formed from disposable and fluid absorbent material. The cleansing mechanism may further include a mechanism for statically mating the auxiliary conduit to the primary conduit such that the primary and auxiliary conduits advantageously and effectively remain in static and fluid communication during operating conditions.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
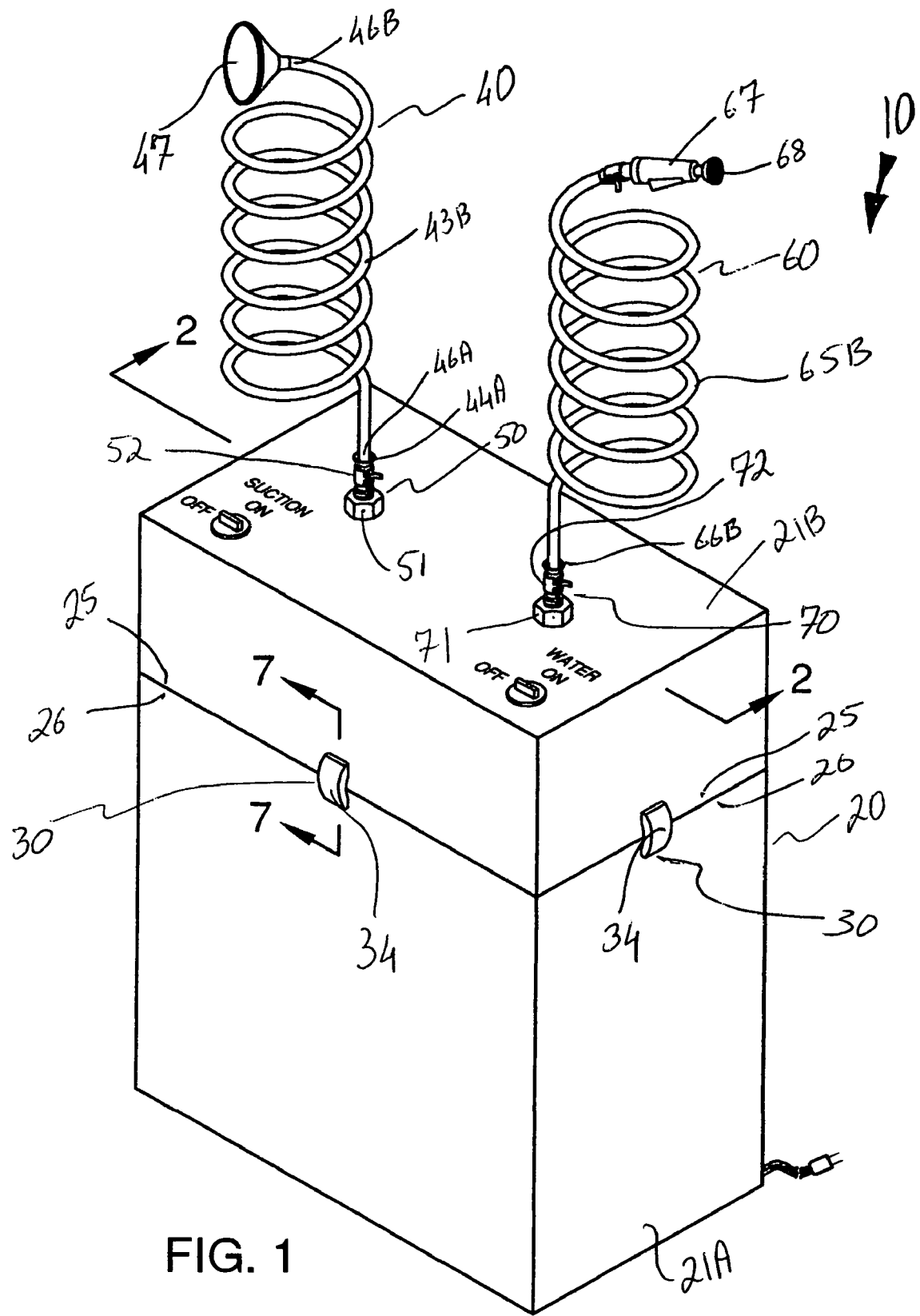
FIG. 1 is a perspective view showing a portable collection and cleansing device, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The device of this invention is referred to generally in FIGS. 1-7 by the reference numeral 10 and is intended to provide a portable collection and cleansing device. It should be understood that the device 10 may be used to cleanse and collect debris from many different types of surfaces and should not be limited in use to only physically impaired individuals.

Figure 2:
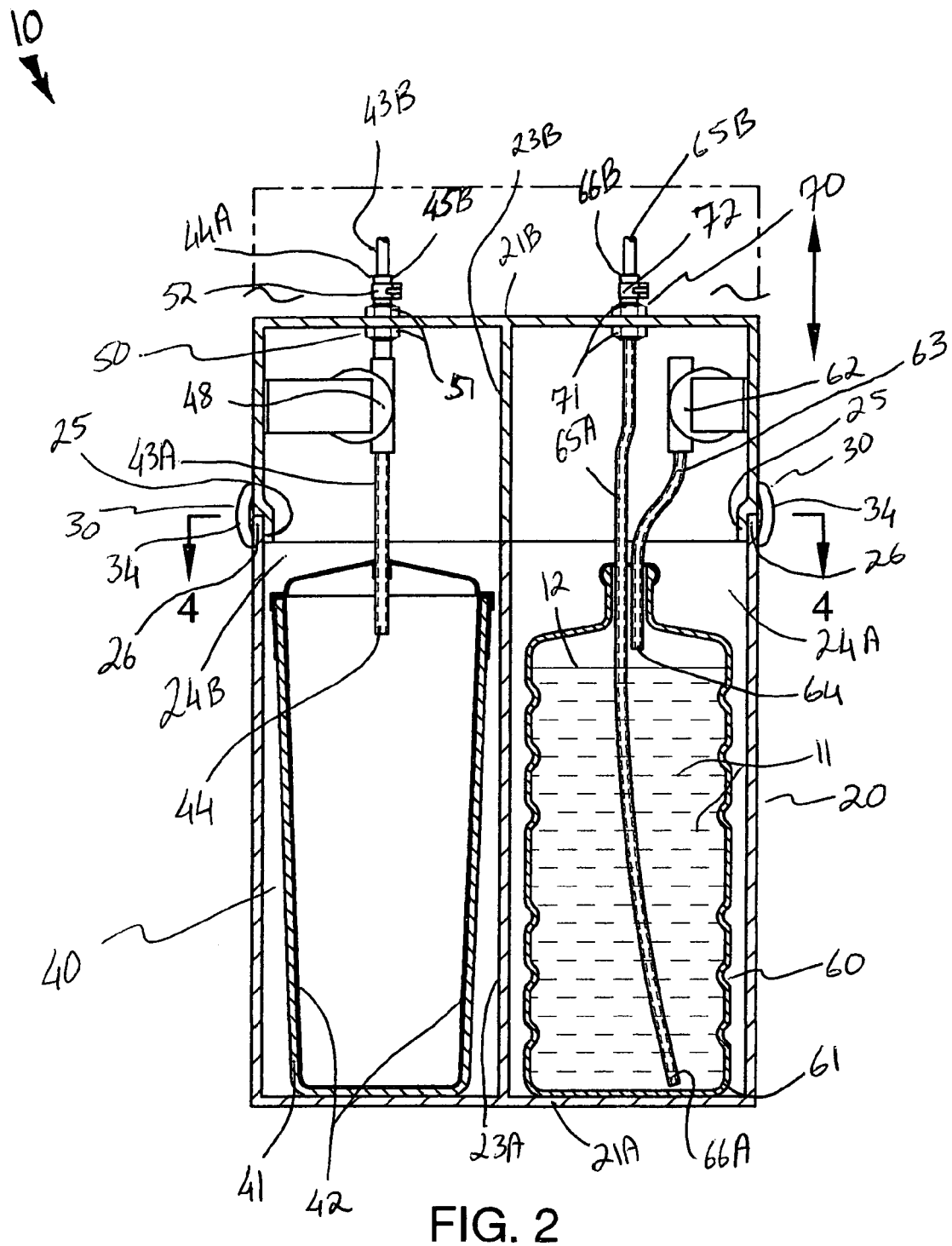
FIG. 2 is a cross-sectional view of the device shown in FIG. 1, taken along line 2-2.
Figure 4:
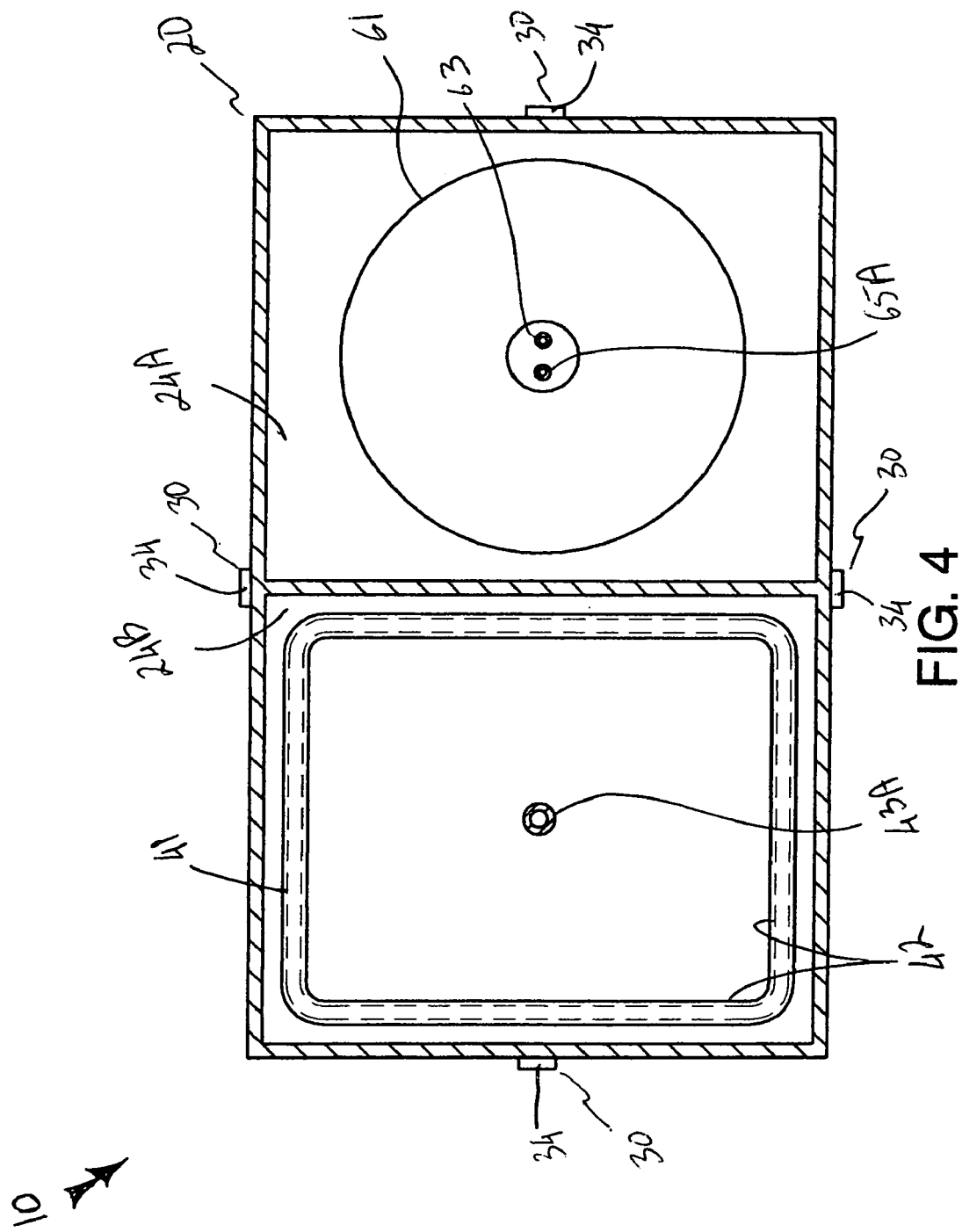
FIG. 4 is a cross-sectional view of the housing shown in FIG. 2, taken along line 4-4.
Figure 5:
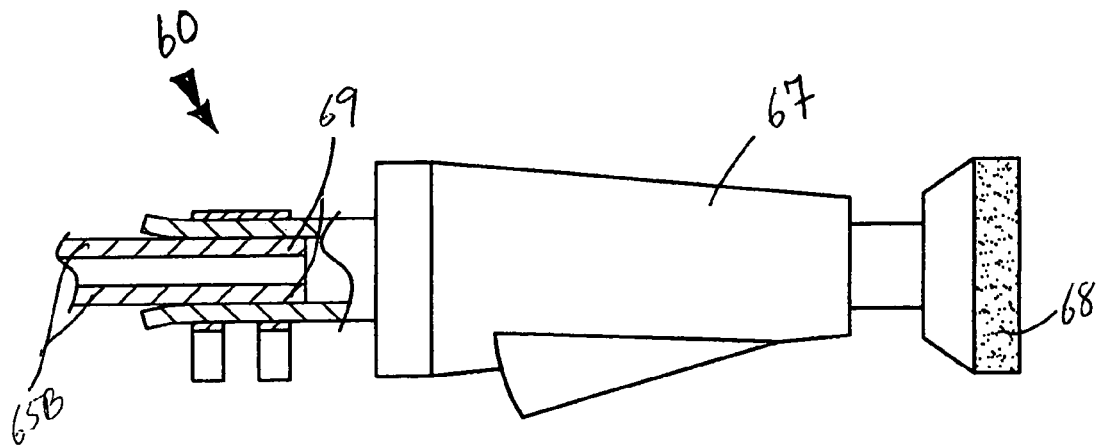
FIG. 5 is an enlarged and partially exposed side-elevational view of the trigger actuated discharge nozzle shown in FIG. 1.
Figure 6:
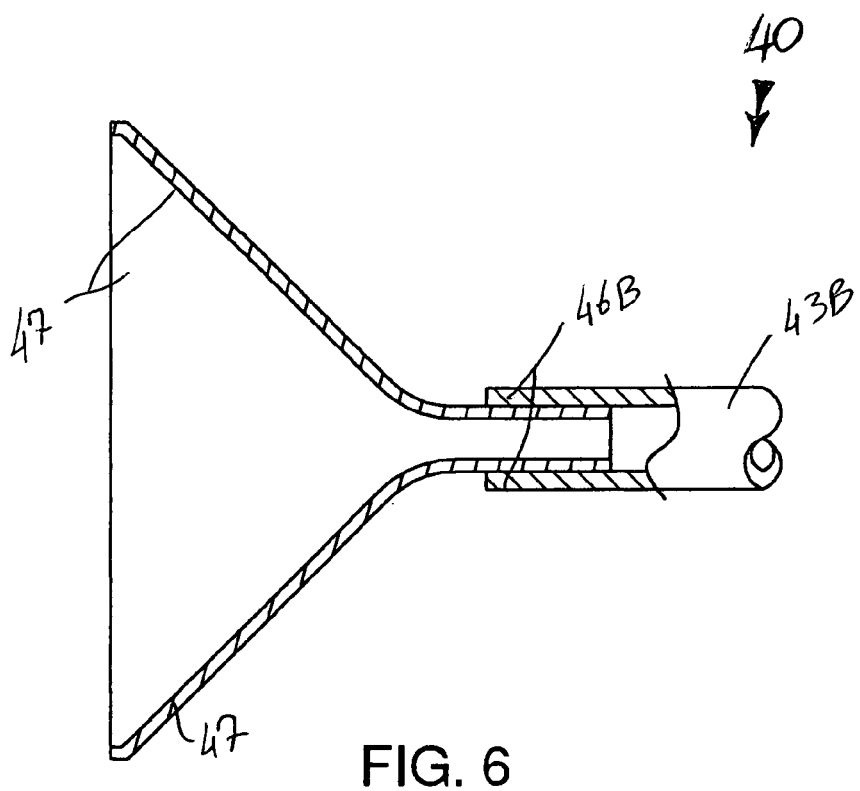
FIG. 6 is an enlarged and partially exposed side-elevational view of the funnel-shaped suction nozzle shown in FIG. 1.
Figure 7:
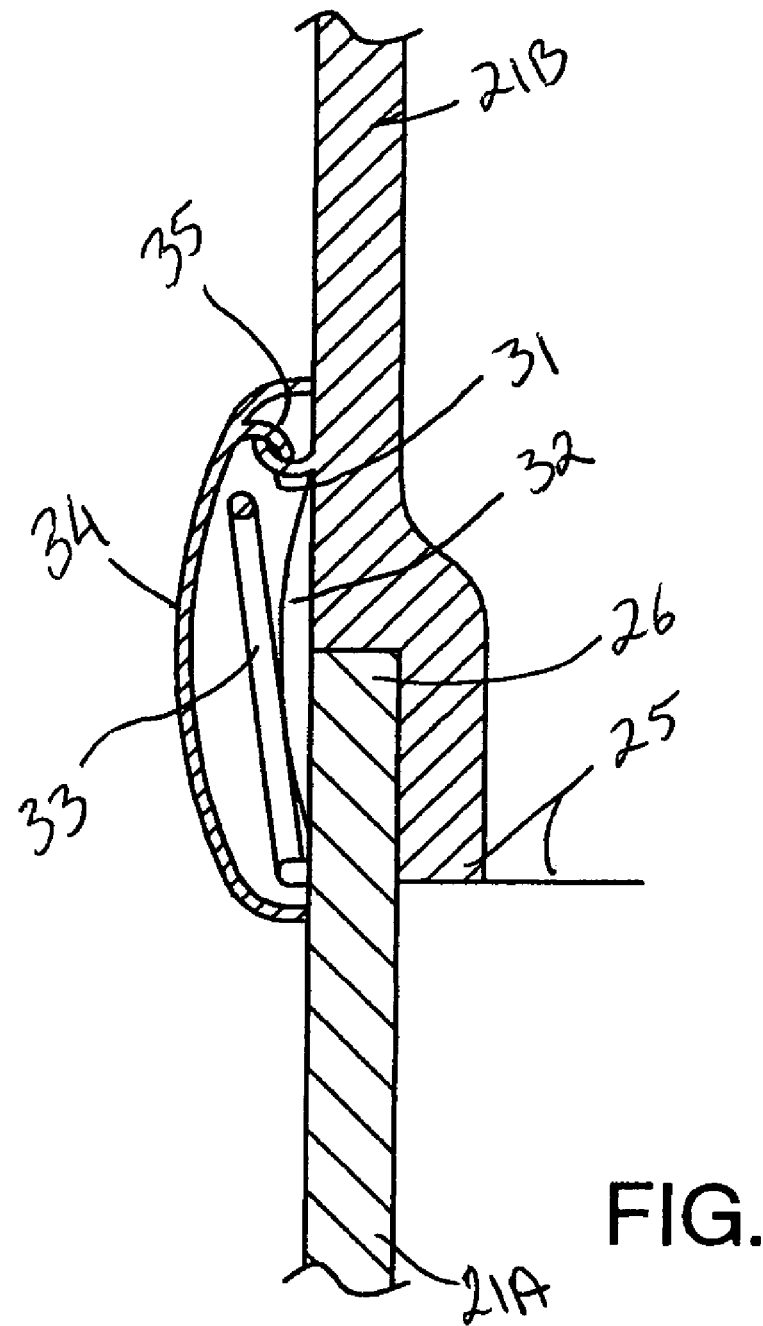
FIG. 7 is a cross-sectional view of one locking mechanism fasteners shown in FIG. 1, taken along line 7-7.

Referring initially to FIGS. 1, 2 and 4, the device 10 includes a housing 20 that is suitably sized and shaped for advantageously and conveniently being transported between remote locations by an operator, thus not limiting the user to their bed or another single location. Such a housing 20 includes a base member 21A and a cover member 21B removably conjoinable directly, with no intervening elements, therewith. The base member 21A includes an open top end 22 and further includes a linear divider 23A centrally position within a cavity of the base member 21A for effectively defining a pair of isolated and coextensively shaped chambers 24 within the housing 20. The cover member 21B includes a divider 23B directly mateable, with no intervening elements, with the divider 23A of the base member 21A when the cover member 21B is attached to the base member 21A. This is an important feature for ensuring a complete isolation of the chambers 24 from each other so that items housed within one chamber 24A (described herein below) cannot contaminate items housed in the another chamber 24B (described herein below) and vice versa.

Referring to FIGS. 1, 2, 4 and 7, a mechanism 30 is included for locking the cover member 21B to the base member 21A, which is essential such that one of the chambers 24A effectively maintains a constant air pressure level greater than an ambient air pressure level surrounding the one chamber 24A. Such a locking mechanism 30 includes a first plurality of fingers 31 and a plurality of shoulder members 32 monolithically formed at predetermined points along a bottom edge 25 of the cover member 21B. A plurality of cams 33 are statically connected directly, with no intervening elements, subjacent to a top edge 26 of the base member 21A and at positions corresponding to the location of the shoulder members 32.

Such cams 33 are slidably engageable with the shoulder members 32, which is essential for temporarily preventing lateral and vertical movement of the cover member 21B with respect to the base member 21A. A plurality of cover members 34 are pivotally connected to the base member 21A subjacent to the plurality of cams 33. Such cover members 34 include a second plurality of fingers 35 that are selectively engageable with the first plurality of fingers 31 for advantageously and effectively locking the cover member 21B in a static relationship with the base member 21A. This is a vital feature for preventing the contents of the device 10 from spilling in the event that the housing 20 is inadvertently knocked over during operating conditions.

Referring to FIGS. 1, 2, 3, 4 and 6, a mechanism 40 is included for collecting body excrements from the patient. Such a collecting mechanism 40 is in fluid communication with another one 24B of the chambers 24 wherein the body excrements are advantageously automatically deposited therein without directly contacting a caregiver. This is a critical feature for improving the sanitary conditions of both the patient and their caregiver(s). The collecting mechanism 40 includes a waste container 41 removably positional within the other chamber 24B and a disposable waste bag 42 removably nested within the waste container 41. Such a waste bag 42 is formed from fluid-impermeable material, which is vital and advantageous for preventing fluid and solid excrements stored therein from leaking out off the waste bag 42. The waste bag 42 further allows for quick and convenient disposal of waste materials once the waste bag 42 is filled to capacity.

Figure 3:
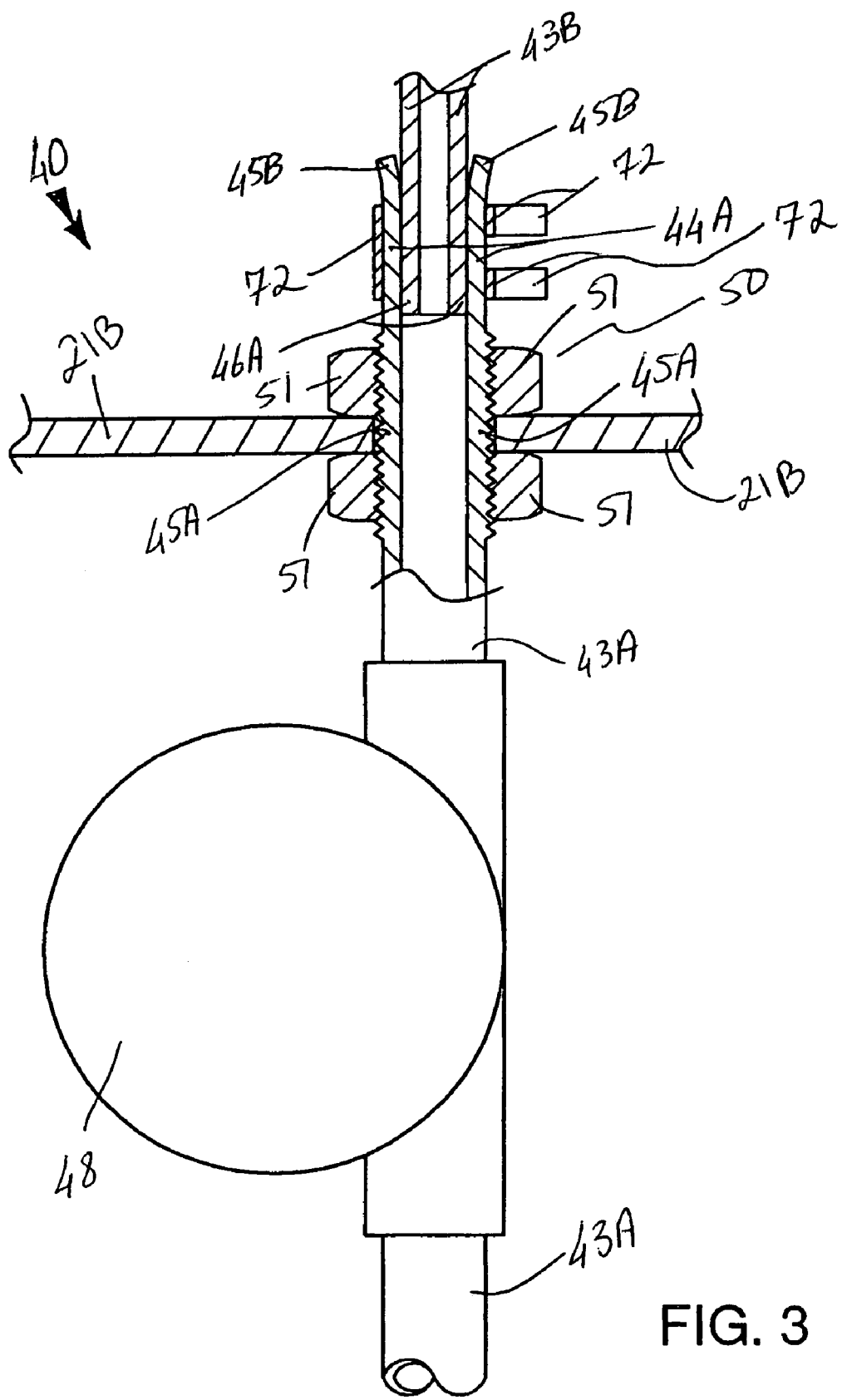
FIG. 3 is an enlarged and partially exposed side-elevational view of the collecting means air pump shown in FIG. 2.

Referring to FIGS. 1, 2 and 3, a primary conduit 43A is formed from deformably resilient material and is channeled through the cover member 21B. Such a primary conduit 43A has a linear shape and axially opposed end portions 44 seated within the waste bag 42 and disposed to an exterior of the cover member 21B. The primary conduit 43A has a threaded outer portion 45A confronting the cover member 21B and has a flanged upper end portion 45B situated to an exterior of the housing 20, as is best shown in FIG. 3. An auxiliary conduit 43B is formed from disposable material and has opposed end portions 46A, 46B slidably engageable with one end portion 44A of the primary conduit 43A and disposed to an exterior of the cover member 21B respectively.

Referring to FIGS. 2 and 3, the primary conduit 43A includes mechanism 50 for statically mating with the auxiliary conduit 43B such that the primary 43A and auxiliary 43B conduits remain in fluid communication during operating conditions. This is an essential feature for preventing the collecting mechanism 40 thus advantageously preventing the collecting mechanism 40 from loosing suction capabilities. Such a mating mechanism 50 includes a plurality of fasteners 51 threadably connected directly, with no intervening elements, to the threaded outer surface 45A of the primary conduit 43A, which is vital such that the primary conduit 43A is advantageously and effectively prohibited from telescopically sliding through the cover member 21B. A clamp 52 is directly positioned, with no intervening elements, about the flanged end portion 45B of the primary conduit 43A. Such a clamp 52 is important for biasing the flanged portion 45B to a compressed position, effectively crimping the primary conduit 43A about the auxiliary conduit 43B, as is best shown in FIG. 3.

Referring to FIGS. 1, 2, 3 and 6, the collecting mechanism 40 further includes a funnel-shaped suction nozzle 47 formed from disposable material and removably attached to a distal end portion 46B of the auxiliary conduit 43B. The larger collecting area of a funnel shaped suction nozzle 47 advantageously eliminates the need for a user to hold the suction nozzle 47 directly against their skin, which does away with the painful suction bruises caused in those particularly sensitive skin areas by the conventional devices known in the prior art. An air pump 48 is directly and operably coupled, with no intervening elements, to the primary conduit 43A. Such an air pump 48 is seated within the housing 20 and is selectively adaptable between operating and non-operating modes for facilitating the removal of body excrements from the patient.

Referring to FIGS. 1, 2, 4 and 5, a mechanism 60 is included for cleansing a selected portion of the patient. Of course, the cleansing mechanism 60 may be used to clean a variety of alternate surfaces, as is obvious to a person of ordinary skill in the art. Such a cleansing mechanism 60 is in fluid communication with the one chamber 24A. The cleansing mechanism 60 and the collecting mechanism 40 are independently and simultaneously operable, which is a crucial and advantageous feature such that a group of care givers can contemporaneously service the patient. The collecting 40 and cleansing 60 mechanisms are further electrically mated to an external power supply source. The cleansing mechanism 60 includes a collapsible vessel 61 seated within the one chamber 24A. Such a vessel 61 contains a predetermined quantity of fluid 11 maintained at the air pressure level. An air supply source 62 is mated within the housing 20 and includes a conduit 63 in fluid communication with an interior of the vessel 61. Such a conduit 63 has a bottom end portion 64 positioned above a water line 12 of the vessel 61.

Referring to FIGS. 1, 2 and 4, a primary conduit 65A has opposed end portions 66A, 66B submerged within the vessel 61 and disposed to an exterior of housing 20 respectively. An auxiliary conduit 65B is in fluid communication with the primary conduit 65A, which is essential and advantageous for effectively directing fluid 11 away from the housing 20. A trigger-actuated discharge nozzle 67 is directly connected, with no intervening elements, to one end portion 69 of the auxiliary conduit 65B wherein an exit flow rate of the fluid 11 can conveniently be controlled at a greater speed than a flow rate of the fluid 11 entering the primary conduit 65A. Such a discharge nozzle 67 includes a scrubbing pad 68 removably attached directly, with no intervening elements, thereto. The scrubbing pad 68 is formed from disposable and fluid absorbent material. This is an important feature for allowing a care giver to conveniently discard of a scrubbing pad 68 after being used to effectively remove solid excrement and other body soils from a patient.

Referring to FIG. 2, the cleansing mechanism 60 further includes a mechanism 70 for statically mating the auxiliary conduit 65B to the primary conduit 65A such that the primary 65A and auxiliary 65B conduits advantageously and effectively remain in static and fluid communication during operating conditions. This is an essential feature for preventing a fluid leak from developing between the primary 65A and secondary 65B conduits, thus giving the user and the caregiver peace of mind and increasing the usefulness of the device 10. Such a mating mechanism 70 includes a plurality of fasteners 71 threadably connected directly, with no intervening elements, to the threaded outer surface (not shown) of the primary conduit 65A, which is vital such that the primary conduit 65A is advantageously and effectively prohibited from telescopically sliding through the cover member 21B. A clamp 72 is directly positioned, with no intervening elements, about the flanged end portion 66B of the primary conduit 65A. Such a clamp 72 is important for biasing the flanged portion 66B to a compressed position, effectively crimping the primary conduit 65A about the auxiliary conduit 65B, as is best shown by the example in FIG. 3 for the mating mechanism 50 of the collecting mechanism 40.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A portable device for collecting body excrements and promoting hygiene for bed-ridden patients, said device comprising:

a housing suitably sized and shaped for being transported between remote locations by an operator, said housing including a base member and a cover member removably conjoinable directly therewith, said base member including an open top end and further including a linear divider centrally position within a cavity of said base member for defining a pair of isolated and coextensively shaped chambers within said housing, said cover member including a divider directly mateable with said divider of said base member when said cover member is attached to said base member;

means for locking said cover member to said base member;

means for collecting body excrements from the patient, said collecting means being in fluid communication with another said chambers wherein the body excrements are automatically deposited therein without directly contacting a caregiver; and means for cleansing a selected portion of the patient, said cleansing means being in fluid communication with said one chamber, wherein one of said chambers maintains a constant air pressure level greater than an ambient air pressure level surrounding said one chamber when said cleansing means introduces air into said one chamber;

wherein said cleansing means and said collecting means are independently and simultaneously operable such that a group of care givers can contemporaneously service the patient;

wherein said collecting and cleansing means are electrically mated to an external power supply source.

2. The device of claim 1, wherein said collecting means comprises:

a waste container removably positional within said another chamber;

a disposable waste bag removably nested within said waste container, said waste bag being formed from fluid-impermeable material;

a primary conduit formed from deformably resilient material and channeled through said cover member, said primary conduit having a linear shape and axially opposed end portions seated within said waste bag and disposed exterior of said cover member, said primary conduit having a threaded outer portion confronting said cover member, said primary conduit having a flanged upper end portion situated exterior of said housing;

an auxiliary conduit formed from disposable material and having opposed end portions seated within said waste bag and disposed exterior of said cover member respectively;

a funnel-shaped suction nozzle formed from disposable material and removably attached to a distal end portion of said auxiliary conduit;

wherein said primary conduit includes means for statically mating with said auxiliary conduit such that said primary and auxiliary conduits remain in fluid communication during operating conditions; and an air pump directly and operably coupled to said primary conduit, said air pump being seated within said housing and selectively adaptable between operating and non-operating modes for facilitating the removal of body excrements from the patient.

3. The device of claim 2, wherein said mating means comprises:

a plurality of fasteners threadably connected directly to said threaded outer surface of said primary conduit such that said primary conduit is prohibited from telescopically sliding through said cover member; and a clamp directly positioned about said flanged end portion of said primary conduit, said clamp biasing said flanged portion to a compressed position and crimping said primary conduit about said auxiliary conduit.

4. The device of claim 1, wherein said cleansing means comprises:

a collapsible vessel seated within said one chamber, said vessel containing a predetermined quantity of fluid maintained at the air pressure level;

an air supply source mated within said housing and including a conduit in fluid communication with an interior of said vessel, said conduit having a bottom end portion positioned above a water line of said vessel;

a curvilinear primary conduit having longitudinal length spanning an entire longitudinal length of said vessel, said curvilinear primary conduit having opposed end portions submerged within said vessel and disposed exterior of housing respectively;

a secondary conduit in fluid communication with said curvilinear primary conduit for directing fluid away from said housing;

a trigger-actuated discharge nozzle directly connected to said secondary conduit wherein an exit flow rate of the fluid can be controlled at a greater speed than a flow rate of the fluid entering said curvilinear primary conduit.

5. The device of claim 4, wherein said discharge nozzle comprises: a scrubbing pad removably attached directly thereto, said scrubbing pad being formed from disposable and fluid absorbent material.

6. The device of claim 4, wherein said cleansing means further comprises:

means for statically mating with said secondary conduit to said curvilinear primary conduit such that said curvilinear primary and secondary conduits remain in static and fluid communication during operating conditions.

* * * * *